United States Patent
Sundermann et al.

(10) Patent No.: US 6,784,175 B2
(45) Date of Patent: Aug. 31, 2004

(54) USE OF SUBSTITUTED 1-AMINO-5-PHENYLPENTANE-3-OL AND/OR 1-AMINO-6-PHENYLHEXANE-3-OL COMPOUNDS AS MEDICAMENTS

(75) Inventors: Bernd Sundermann, Aachen (DE); Werner Englberger, Stolberg (DE); Boris Chizh, Whittlesford (GB)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/276,617

(22) PCT Filed: May 10, 2001

(86) PCT No.: PCT/EP01/05349

§ 371 (c)(1),
(2), (4) Date: Nov. 18, 2002

(87) PCT Pub. No.: WO01/89505

PCT Pub. Date: Nov. 29, 2001

(65) Prior Publication Data

US 2003/0181450 A1 Sep. 25, 2003

(30) Foreign Application Priority Data

May 22, 2000 (DE) .......................................... 100 25 238

(51) Int. Cl.[7] .................. A61K 31/137; A61K 31/4453; A61K 31/404; A61K 31/5375; A61P 25/00
(52) U.S. Cl. .................... 514/238.8; 514/317; 514/428; 514/653; 544/173; 546/240; 548/570; 564/355; 564/361; 564/366; 564/503
(58) Field of Search .............................. 514/238.8, 317, 514/428, 653; 544/173; 546/240; 548/570; 564/355, 361, 366, 503

(56) References Cited

U.S. PATENT DOCUMENTS 4,017,637 A    4/1977   Yardley et al. ............. 424/311

FOREIGN PATENT DOCUMENTS

EP          1043307 A2      10/2000
WO        WO 92/05169       4/1992

OTHER PUBLICATIONS

"Zur Nootropikabewertung für die Praxis", IHL et al., Nervenarzt, Bd. 68, Nr. 11, 1997.
"General Formula II", Applied Chem. 106, 1994, pp. 2531–2533.
"Cheng–Prusoff Equation", Cheng et al., Biochemical Pharmacology, vol. 22, pp. 3099–3108.
"Synlett", 1997, pp. 974–976.
Acta Chemica Scandinavica B 38, 1984, pp. 49–53.
"Methods of Organic Chemistry", Houben–Weyl, 1995, vol. E21, p. 1925–29.
"Synthesis" 1975, pp. 617–630.

Primary Examiner—Brian Davis
(74) Attorney, Agent, or Firm—Perman & Green LLP

(57) ABSTRACT

The use of at least one substituted 1-amino-5-phenylpentane-3-ol and/or 1-amino-6-phenylhexane-3-ol compound and/or one of the enantiomers thereof and/or one of the diastereomers thereof and/or one of the physiologically acceptable salts thereof for producing a medicament that has an N-methyl-D-aspartate-(NMDA)-antagonistic effect.

33 Claims, No Drawings

USE OF SUBSTITUTED 1-AMINO-5-PHENYLPENTANE-3-OL AND/OR 1-AMINO-6-PHENYLHEXANE-3-OL COMPOUNDS AS MEDICAMENTS

This application claims the benefit of the earlier filed International Application No. PCT/EP01/05349, International Filing Date, May 10, 2001, which designated the United States of America, and which international application was published under PCT Article 21(2) as WO Publication No. WO 01/89505 A1.

The invention relates to the use of at least one substituted 1-amino-5-phenylpentane-3-ol and/or 1-amino-6-phenylhexane-3-ol compound and/or one of the enantiomers thereof and/or one of the diastereomers thereof and/or one of the corresponding physiologically tolerable salts thereof in the manufacture of a medicament with an N-methyl-D-aspartate (NMDA) antagonistic effect.

Knowledge of the physiological significance of ion channel selective substances has been gained through the development of the patch clamp technique. Of particular significance is the NMDA ion channel, through which a considerable proportion of synapse communications runs. The exchange of calcium ions between a neuronal cell and its environment is controlled by this ion channel. The effect of NMDA antagonists on the flow of calcium ions into the interior of the cell can be demonstrated using the patch clamp technique.

In an inactivated state, the NMDA ion channels are closed by single magnesium ions which are inside the channel but cannot pass therethrough owing to their size. In an activated state, the smaller calcium and sodium ions can pass through the channel. The (+)-MK801 binding site of the NMDA ion channel (ionotropic NMDA receptor) is also inside this membrane protein. Substances with an NMDA anatagonist effect, such as phencyclidine (PCP), ketamine or MK801 occupy this binding site (so-called "channel blockers") and thus close the NMDA ion channel in question.

NMDA ion channels play an important role in many physiological and pathophysiological processes, such as, for example, epilepsy, schizophrenia, neurodegenerative diseases, especially in Alzheimer's disease, Huntington's disease and Parkinson's disease, cerebral ischaemia and infarction, psychoses caused by raised amino acid level, cerebral oedema, under-supply of the central nervous system, in particular with hypoxia and anoxia, AIDS dementia, encephalomyelitis, Tourette's syndrome, perinatal asphyxia and tinnitus.

The aim of this invention was therefore to make medicaments available which exhibit an NMDA antagonist effect and are therefore suitable for the preventative treatment of cerebrovascular attacks (strokes) and/or the treatment of epilepsy and/or schizophrenia and/or neurodegenerative diseases, in particular Alzheimer's disease, Huntington's disease or Parkinson's disease and/or cerebral ischaemia and/or cerebral infarction and/or psychoses caused by raised amino acid level and/or cerebral oedema and/or under-supply of the central nervous system, in particular hypoxia and/or anoxia and/or AIDS dementia and/or encephalomyelitis and/or Tourette's syndrome and/or perinatal asphyxia and/or tinnitus.

Surprisingly, it was found that substituted 1-amino-5-phenylpentane-3-ol and 1-amino-6-phenylhexane-3-ol compounds of general formula I below and the enantiomers, diastereomers and physiologically tolerable salts thereof exhibit a marked NMDA antagonistic effect and therefore are highly suitable for influencing the above mentioned physiological and pathophysiological processes.

The object of this invention is the use of at least one substituted 1-amino-5-phenylpentane-3-ol and/or 1-amino-6-phenylhexane-3-ol compound of general formula I,

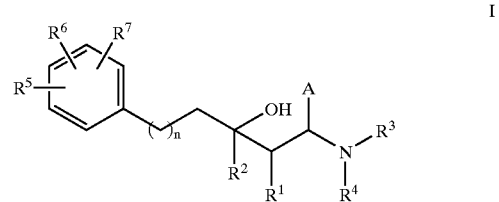

where n=1 or 2,

- group A represents an optionally substituted aryl or heteroaryl group,
- groups $R^1$ and $R^2$, the same or different, stand for a $C_{1-6}$ alkyl group, preferably a $C_{1-3}$ alkyl group, or groups $R^1$ and $R^2$ together form a $(CH_2)_{2-6}$ chain, which may also be phenyl substituted or may be attached to a phenyl ring to form a bicyclic system in which the cyclic aliphatic moiety and the phenyl ring share two carbon atoms.
- groups $R^3$ and $R^4$, the same or different, stand for a $C_{1-6}$ alkyl group, preferably a $C_{1-3}$ alkyl group, preferable a $C_{1-3}$ alkyl group, an optionally substituted aryl group or optionally substituted aryl group which is bound via a $C_{1-3}$ alkylene group, or groups $R^3$ and $R^4$ together represent $(CH_2)_{3-6}$ or $CH_2CH_2OCH_2CH_2$,
- groups $R^5$, $R^6$ and $R^7$, the same or different, represent H, F, Cl, Br, I, $CF_3$, $OR^8$, $SO_2CH_3$, $SO_2CF_3$, phenyl, CN, $NO_2$ or a $C_{1-6}$ alkyl group, preferably a $C_{1-3}$ alkyl group,
- group $R^8$ stands for H, a $C_{1-6}$ alkyl group, preferably a $C_{1-3}$ alkyl group, an optionally substituted aryl group, an optionally substituted heteroaryl group or for a optionally substituted aryl or heteroaryl group which is bound via a $C_{1-3}$ alkylene group,
- and/or one of the enantiomers thereof and/or one of the diastereomers thereof and/or a corresponding physiologically tolerable salt for the manufacture of a medicament with an NMDA antagonistic effect.

Physiologically tolerable salts of the compounds of general formula I and/or enantiomers thereof and/or diastereomers thereof may be hydrochloride, hydrobromide, sulphate, sulphonate, phosphate, tartrate, embonate, formate, acetate, propionate, benzoate, oxalate, succinate, citrate, glutamate, fumarate, aspartate, glutarate, stearate, butyrate, malonate, lactate, mesylate or a mixture of at least two of these salts.

Alkyl groups means branched, unbranched and cyclic hydrocarbon groups, which can also be substituted at least simply, preferably with a halogen group and/or a hydroxyl group, particularly preferably with fluorine and/or a hydroxyl group. If these alkyl groups contain more than one substituent, then these substituent may be the same or different. The alkyl groups are preferably methyl, ethyl, propyl, 1-methylethyl, butyl, 1-methylpropyl, 2-methylpropyl, 1,1-dimethylethyl, pentyl, 1,1-dimethylpropyl, 1,2-diemethylpropyl, 2,2-dimethylpropyl, hexyl, 1-methylpentyl, cyclopropyl, cyclopropylmethyl, 2-methylcyclopropyl, cyclopentyl, cyclohexyl, $CHF_2$, $CF_3$ or $CH_2OH$.

An aryl group also means at least a phenyl or naphthyl group substituted simply with an $OR^8$, halogen, preferably F and/or Cl, CN, NO$_2$, C$_{1-6}$ alkyl or phenyl group, whereby the R$^8$ group has the meaning according to general formula I. The phenyl groups can also be condensed with further rings.

A heteroaryl group also means 5- or 6-member, unsaturated, heterocyclic compounds, optionally containing fused aryl groups, which contain at least one heteroatom, preferably nitrogen, oxygen or sulphur, particularly preferably nitrogen or oxygen and which optionally also can be substituted at least simply with an OR$^8$, halogen, preferably F and/or Cl, CN, NO$_2$, C$_{1-6}$ alkyl or phenyl group, whereby the R$^8$ group has the meaning according to general formula I. Preferred, optionally substituted, heteroaryl groups are furan, thiophene, pyrrole, pyridine, pyrimidine, quinoline, isoquinoline, phthalazine or quinazoline.

In a preferred embodiment of this invention, at least one compound of general formula I is used, in which groups R$^1$ and R$^2$ together form a (CH$_2$)$_{2-6}$ chain, which can also be phenyl substituted or attached to a phenyl ring to form a bicyclic system in which the cyclic aliphatic moiety and the phenyl ring share two carbon atoms and groups R$^3$ to R$^8$ and A have the meaning according to general formula I.

Also preferable is the use of at least one compound of general formula I, in which A means an unsubstituted or substituted phenyl, thiophenyl or furyl group and groups R$^1$ to R$^8$ have the meaning according to general formula I.

Also preferable is the use of at least one compound of general formula I, in which groups R$^5$ to R$^7$, the same or different, mean H, a halogen or a CF$_3$ group and groups R$^1$ to R$^4$, R$^8$ and A have the meaning according to general formula I.

Also preferable is the use of at least one compound of general formula I, in which the phenyl ring in general formula I is substituted once or twice in an ortho-position and groups R$^1$ to R$^8$ and A have the meaning according to general formula I.

Also preferable is the use of at least one compound of general formula I, in which A represents a phenyl ring, which is substituted once or twice in an ortho-position and groups R$^1$ to R$^8$ have the meaning according to general formula I.

In a particularly preferred embodiment of this invention, at least one compound of general formula I is used, in which groups R$^1$ and R$^2$ together form a cyclohexyl ring, which can also be phenyl substituted or benzo-condensed, A means an unsubstituted or substituted phenyl, thiophenyl or furyl group and groups R$^3$ to R$^8$ have the meaning according to general formula I.

Also particularly preferable is the use of at least one compound of general formula I, in which A represents a phenyl ring, which is substituted once or twice in an ortho-position and in which the phenyl ring in general formula I is substituted once or twice in an ortho-position and groups R$^1$ to R$^8$ have the meaning according to general formula I.

Quite particularly preferable is the use of at least one of the following compounds of general formula I:

2-(dimethylaminophenylmethyl)-1-phenethylcyclohexanol or the corresponding hydrochloride, 2-[(2-chlorophenyl)dimethylaminomethyl]-1-phenethylcyclohexanol or the corresponding hydrochloride, 2-[(2-bromophenyl)dimethylaminomethyl]-1-phenethylcyclohexanol or the corresponding hydrochloride, 2-[dimethylamino-(3-methoxyphenyl)methyl]-1-phenethylcyclohexanol or the corresponding hydrochloride, 2-(dimethylamino-o-tolylmethyl)-1-phenethylcyclohexanol or the corresponding hydrochloride 2-(dimethylaminophenylmethyl)-1-(3-phenylpropyl)cyclohexanol or the corresponding hydrochloride, 2-(dimethylaminophenylmethyl)-1-[2-(2-fluorophenyl)ethyl]cyclohexanol or the corresponding hydrochloride, 2-[dimethylamino-(2-fluorophenyl)methyl]-1-phenethylcyclohexanol or the corresponding hydrochloride, 2-[(2-chlorophenyl)dimethylaminomethyl]-1-[2-(4-fluorophenyl)ethyl]cyclohexanol or the corresponding hydrochloride, 2-[(2-chlorophenyl)dimethylaminomethyl]-1-[2-(2-fluorophenyl)ethyl]cyclohexanol or the corresponding hydrochloride, 2-[(2-chlorophenyl)dimethylaminomethyl]-1-[2-(3-fluorophenyl)ethyl]cyclohexanol or the corresponding hydrochloride, 1-[2-(2-chlorophenyl)ethyl]-2-(dimethylaminophenylmethyl)cyclohexanol or the corresponding hydrochloride, 1-[2-(3-chlorophenyl)ethyl]-2-(dimethylaminophenylmethyl)cyclohexanol or the corresponding hydrochloride, 1-phenethyl-2-(phenylpiperidine-1-yl-methyl)cyclohexanol or the corresponding hydrochloride, 1-[2-(2-chlorophenyl)ethyl]-2-(dimethylamino-o-tolylmethyl)cyclohexanol or the corresponding hydrochloride, 1-[2-(3-chlorophenyl)ethyl]-2-(dimethylamino-o-tolylmethyl)cyclohexanol or the corresponding hydrochloride, 2-[dimethylamino-(2-fluorophenyl)methyl]-1-[2-(4-fluorophenyl)ethyl]cyclohexanol or the corresponding hydrochloride, 2-(dimethylamino-o-tolylmethyl)1-[2-(4-fluorophenyl)ethyl]cyclohexanol or the corresponding hydrochloride, 1-[2-(2-chlorophenyl)ethyl]-2-(dimethylamino-(2-fluorophenyl)methyl]cyclohexanol or the corresponding hydrochloride, 1-[2-(2-chlorophenyl)ethyl]-2-(dimethylamino-m-tolylmethyl)cyclohexanol or the corresponding hydrochloride, 1-[2-(3-chlorophenyl)ethyl]-2-(dimethylamino-(2-fluorophenyl)methyl]cyclohexanol or the corresponding hydrochloride, 1-[2-(2-chlorophenyl)ethyl]-2-(dimethylamino-(3-fluorophenyl)methyl]cyclohexanol or the corresponding hydrochloride, 1-[2-(2-chlorophenyl)ethyl]-2-(pyrrolidine-1-yl-o-tolylmethyl)cyclohexanol or the corresponding hydrochloride, 1-[2-(2-chlorophenyl)ethyl]-2-(morpholine-4-yl-o-tolylmethyl)cyclohexanol or the corresponding hydrochloride, 1-[2-(2-chlorophenyl)ethyl]-2-(piperidine-1-yl-o-tolylmethyl)cyclohexanol or the corresponding hydrochloride, 1-[2-(3-chlorophenyl)ethyl]-2-(dimethylamino-o-tolylmethyl)cyclohexanol or the corresponding hydrochloride, 2-[dimethylamino-(2-trifluoromethylphenyl)methyl]-1-phenethylcyclohexanol or the corresponding hydrochloride, 2-[dimethylamino-(2-methoxyphenyl)methyl]-1-[2-(2-fluorophenyl)ethyl]cyclohexanol or the corresponding hydrochloride, 2-[dimethylamino-(2-fluorophenyl)methyl]-1-[2-(2-fluorophenyl)ethyl]cyclohexanol or the corresponding hydrochloride,
2-(dimethylamino-o-tolylmethyl)-1-[2-(2-fluorophenyl)ethyl]cyclohexanol or the corresponding hydrochloride,
1-[2-(2-fluorophenyl)ethyl]-2-(pyrrolidine-1-yl-o-tolylmethyl)cyclohexanol or the corresponding hydrochloride,
2-[(2-bromophenyl)dimethylaminomethyl]-1-[2-(2-chlorophenyl)ethyl]cyclohexanol or the corresponding hydrochloride,
2-[(2-chlorophenyl)dimethylaminomethyl]-1-[2-(2-chlorophenyl)ethyl]cyclohexanol or the corresponding hydrochloride,
2-[(2-bromophenyl)dimethylaminomethyl]-1-[2-(2-fluorophenyl)ethyl]cyclohexanol or the corresponding hydrochloride,
2-[(2-chlorophenyl)dimethylaminomethyl]-1-(2-o-tolylethyl)cyclohexanol or the corresponding hydrochloride,
2-[(2-chlorophenyl)dimethylaminomethyl]-1-(3-phenylpropyl)cyclohexanol or the corresponding hydrochloride,
2-(dimethylaminophenylmethyl)-1-(2-o-tolylethyl)cyclohexanol or the corresponding hydrochloride,
2-[(2-bromophenyl)dimethylaminomethyl]-1-(2-o-tolylethyl)cyclohexanol or the corresponding hydrochloride,
2-(dimethylamino-o-tolylmethyl)-1-(2-o-tolylethyl)cyclohexanol or the corresponding hydrochloride,
2-[(2-bromophenyl)dimethylaminomethyl]-1-(3-phenylpropyl)cyclohexanol or the corresponding hydrochloride,
2-[(2-chloro4-fluorophenyl)dimethylaminomethyl]-1-[2-(2-fluorophenyl)ethyl]cyclohexanol or the corresponding hydrochloride,
2-[(2-chloro4-fluorophenyl)dimethylaminomethyl]-1-[2-(2-chlorophenyl)ethyl]cyclohexanol or the corresponding hydrochloride,
2-[dimethylamino-(2-fluorophenyl)methyl]-1-(2-o-tolylethyl)cyclohexanol or the corresponding hydrochloride,
2-[dimethylamino-(2-fluorophenyl)methyl]-1-(3-phenylpropyl)cyclohexanol or the corresponding hydrochloride,
2-(dimethylamino-o-tolylmethyl)-1-(3-phenylpropyl)cyclohexanol or the corresponding hydrochloride,
1-[2-(2-chlorophenyl)ethyl]-2-[dimethylamino-(2-trifluoromethylphenyl)methyl]cyclohexanol or the corresponding hydrochloride,
or
2-[dimethylamino-(2-trifluoromethylphenyl)methyl]-1-[2-(2-fluorophenyl)ethyl]cyclohexanol or the corresponding hydrochloride.

A further object of the invention is also the use of at least one substituted 1-amino-5-phenylpentane-3-ol and/or 1-amino-6-phenylhexane-3-ol compound of general formula I for the manufacture of a medicament for the preventative treatment of cerebrovascular attacks (strokes) and/or the treatment of epilepsy and/or schizophrenia and/or neurodegenerative diseases, in particular Alzheimer's disease and/or Huntington's disease and/or Parkinson's disease and/or cerebral ischaemia and/or cerebral infarction and/or psychoses caused by raised amino acid level and/or cerebral oedema and/or under-supply of the central nervous system, in particular hypoxia and/or anoxia and/or AIDS dementia and/or encephalomyelitis and/or Tourette's syndrome and/or perinatal asphyxia and/or tinnitus.

The above mentioned medicament may also contain a mixture of enantiomers of at least one compound of general formula I, whereby the enantiomers in this mixture are not present in equimolar quantities. The relative proportion of one of the enantiomers in such a mixture of enantiomers preferably amounts to 5 to 45 percent by mass.

Preparation of the medicament may involve, along with at least one compound of general formula I, further excipients, such as base materials, fillers, solvents, diluents, colorants and binders. The selection of excipients and the amounts to be used depend on whether the medicament is to be administered orally, intravenously, intraperitoneally, intradermally, intramuscularly, intranasally, buccally or locally. Suitable excipients and their quantities are known to people skilled in the art for each type of administration. For oral administration, medicaments in the form of tablets, lozenges, chewing gums, dragees, capsules, granulates, drops, juices and syrups are suitable, for parenteral, topical and inhalation administration, preferably solutions, suspensions, emulsions, easily reconstituted dry preparations, spheroids, sprays, suppositories or plasters, such as transdermal therapeutic systems, are suitable. For buccal administration, preferably a transmucal therapeutic system is suitable. The compounds of general formula I in depot, in dissolved form or in a plaster, optionally with the addition of a skin penetration medium, are suitable as percutaneous administration forms. Orally or percutaneously applicable preparation forms may release compounds of general formula I with delayed action.

The amount of active ingredient to be given to patients varies according to the patients' weight, the type of administration, the indication and the severity of the illness. Usually, 0.5 to 50 mg per kg of patients' body weight of at least one compound of general formula I is administered.

The substituted 1-amino-5-phenylpentane-3-ol and 1-amino-6-phenylhexane-3-ol compounds of general formula I can be manufactured as described below. The $R^1$ to $R^7$ groups and A have the meaning in accordance with general formula I in the following general formulae II to IX.

Through the conversion of Mannich bases of general formula II

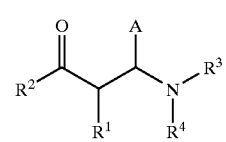

II with substituted Grignard compounds of general formula III

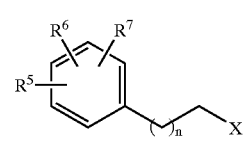

III where n=1 or 2 and X=MgCl, MgBr, MgI or Li, in an aliphatic ether, preferably diethylether and/or tetrahydrofuran, a hydrocarbon, preferably hexane or toluene, or mixtures of hydrocarbons and aliphatic ethers, preferably at temperatures between −70° C. and +110° C., depending on the reaction conditions, preferably tertiary alcohols with the relative configuration of general formula Ia are obtained,

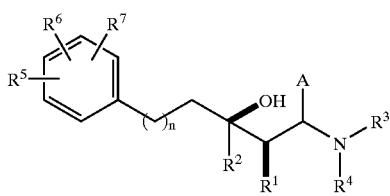

Ia in which the aminoarylmethyl or aminoheteroaryl methyl group is arranged cis to the hydroxyl group if $R^1$ and $R^2$ form a ring system. With open-chain systems, the analogous relative stereo-chemistry is preferably obtained, which is to be specified as anti. The compounds of general formula I can be obtained free from diastereomers by column chromatographic separation or by crystallisation of the salts thereof, for example hydrochlorides.

In accordance with procedures known from the literature (Houben-Weyl—Methods in Organic Chemistry, E21b, 1995, pp 1925–1929), the Mannich bases of general formula II can be obtained by conversion of enamines of general formula IV,

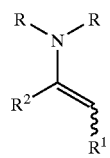

IV with an imminium salt of general formula V,

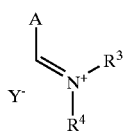

V where Y preferably means Cl⁻, $AlCl_4^-$, Br⁻ or I⁻.

The enamines of general formula IV are obtained in accordance with procedures known from the literature through the conversion of ketones of general formula VI

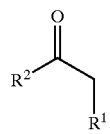

VI with secondary amines, preferably dimethylamine, pyrrolidine, piperidine or morpholine. (Acta Chem. Scand. Vol 38, 1984, pp 49–53). The imminium salts of general formula V are manufactured in accordance with procedures known from the literature through the conversion of animals of general formula VII

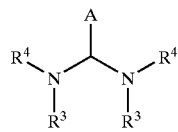

VII with acid chlorides, for example acetyl chloride or thionyl chloride (Houben-Weyl—Methods in Organic Chemistry, E21b, 1995, pp 1925–1929).

The imminium salts of general formula V need not be isolated, but instead can be produced in situ and converted, with enamines of general formula IV, to Mannich bases of general formula II (Applied Chem. 106, 1994, pp 2531–2533). Owing to the enamine-imine tautomerism, which is analogous to keto-enol tautomerism, imines of general formula VIII can be used instead of the enamines of general formula IV,

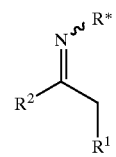

VIII where R* stands for an alkyl or aryl group. Alternatively, ketones of general formula VI can also be converted directly with imminium salts of general formula V.

However, Mannich bases of general formula II can also be manufactured directly by conversion of enamines of general formula IV with an aromatic or heteroaromatic aldehyde of general formula IX

IX and a secondary amine of general formula $HNR^3R^4$ (XI), which may also take the form of the corresponding hydrochloride $HNR^3R^4HCl$, preferably in the presence of triethylamine, chlorotrimethylsilane and sodium iodide (Synlett 1997, pp 974–976).

The Mannich bases of general formula II are obtained using the above mentioned procedures in relation to the reaction conditions, preferably with the relative configuration of general formula IIa,

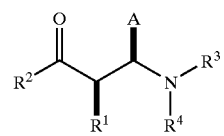

IIa in which the amino group is arranged anti to $R^1$. These compounds of general formula IIa can be obtained free from diastereomers by crystallisation, also of the salts thereof, hydrochlorides for example, or by chromatographic separation.

The representation of Mannich bases of general formula II by 1,4 addition of secondary amines of general formula XI to enones of general formula X,

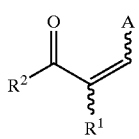

which are obtained from the aldol condensation of ketones of general formula VI with aromatic or heteroaromatic aldehydes of general formula IX, is, on the other hand, less stereoselective (U.S. Pat. No. 4,017,637). This procedure is therefore suitable for the representation of other possible stereoisomers.

If chiral amines are used to represent enamines of general formula IV or imines of general formula VIII, then enantiomer-enriched to enantiomer-free Mannich bases of general formula II may be obtained in the subsequent Mannich reaction (Houben-Weyl—Methods in Organic Chemistry, E21b, 1995, pp 1925–1929).

1-amino-5-phenylpentane-3-ol and 1-amino-6-phenylhexane-3-ol compounds of general formula I, which contain a phenol, can preferably be manufactured from the corresponding methylether compounds with diiusobutyl aluminium hydride in an aromatic hydrocarbon, preferably toluene, at a temperature between 60° C. and 130° C. (Synthesis 1975, pp 617–630).

The compounds of general formula I can be converted with the corresponding acids in a known manner into the physiologically tolerable salts thereof. Salt formation preferably takes place in a solvent, for example diethylether, diisopropylether, alkyl acetate, acetone and/or 2-butanone. Furthermore, trimethylchlorosilane in methylethylketone is suitable for the manufacture of hydrochlorides.

Molecular Biological Research

Research to determine the NMDA antagonistic effect of each compound in general formula I was carried out on cerebral membrane homogenates (homogenate of rat brain without cerebellum, pons and medulla oblongata taken from male Wistar rats (Charles River, Sulzfeld, Germany)).

For this purpose, after separating the cerebellum, pons and medulla oblongata, freshly prepared rat brains were macerated in 50 mmol/l of tris/HCl (pH 7.7) with a Polytron homogeniser (model PT3000, Kinematika AG, Littau, Switzerland) at 6000 revolutions per minute (rpm) for 1 minute with ice cooling and centrifuged for 15 minutes at 4° C. and 60,000 g. After decanting and discarding the supernatant, again placing in 50 mmol/l of tris/HCl (pH 7.7) and macerating the membrane pellet with a homogeniser at 2000 rpm for 1 minute, it was centrifuged again for 15 minutes at 4° C. and 60,000 g. The supernatant was again discarding and the membrane pellet homogenised (2000 rpm for 1 minute) in 50 mmol/l of tris/HCl (pH 7.7) and frozen in aliquots at −70° C.

For the receptor bonding test, each aliquot was defrosted and then centrifuged for 15 minutes at 4° C. and 60,000 g. After decanting and discarding the supernatant, the membrane pellet was taken up with bonding test buffer and homogenised (2000 rpm for 1 minute). The bonding test buffer was 5 mmol/l tris/HCl (pH 7.7) supplemented with 30 μmol/l of glycine and 100 μmol/l of glutamic acid.

1 nmol/l of ($^3$H)-(+)-MK801 ((5R, 10S)-(+)-5-methyl-10,11-dihydro-5H-dibenzo(a,d)cycloheptane-5,10-imine was used as a radioactively marked ligand (NET-972, NEN, Cologne Germany). The proportion of unspecific bonding was determined in the presence of 10 μmol/l of non-radioactively marked (+)-MK801 (RBI/Sigma, Deisenhofen, Germany). In further batches, each of the compounds of general formula I were added in series of concentrations and the displacement of the radioactive ligand out of its specific bond to the NMDA receptor determined. All the batches were subjected to triple determinations. The batches were each incubated for 40 minutes at 25° C. in a water bath and then harvested for determination of the radioactive ligand bound to the cerebral membrane homogenate by means of filtration through glass-fibre filters (GF/B) (Whatman GF/B, Hassel, Munich, Germany). The radioactivity retained by the glass-fibre filter discs was measured in a β counter (Packard TRI-CARB Liquid Scintillation Analyser 2000CA, Packard Instrument, Meriden, Conn. 06450, USA) after adding a scintillator ("Ready Protein" scintillator, Beckmann Coulter GmhH, Krefeld, Germany).

The percentage inhibition of the specific bonding of the ligand ($^3$H)-(+)-MK801 in the presence of 10 μmol/l of each compound of general formula I resulting from the triple batches is used as a measure of the affinity of the compound for the (+)-MK801 binding site of the ionotropic NMDA receptor. From batches with concentration series of these compounds of general formula I, the $IC_{50}$ values (concentration of substituted compounds with 50% displacement of radioactive ligand out of its specific bond) were calculated in accordance with the law of mass action using non-linear regression. From these $IC_{50}$ values, the $K_j$ values were calculated in accordance with the Cheng-Prusoff equation (Y. Cheng, W. H. Prusoff, 1973, Biochem. Pharmacol., 22, pp 3099–3108).

The invention is explained below by means of examples. These examples are used to explain the invention, but they do not restrict the general inventive concept.

EXAMPLES

The yields of the compounds produced are not optimised.
All temperatures are uncorrected.
The stationary phase for column chromatography was silica gel 60 (0.040–0.063 mm) from E. Merck of Darmstadt.
Thin-layer chromatography was undertaken with HPTLC chromatoplates, silica gel 60 F 254 from E. Merck of Darmstadt.
The mixing ratios of the mobile solvent for all the chromatography are always given in volume/volume.
The resolutions of racemates were carried out on a Chiracel OD column or on a ChiraPak AD column with a guard column produced by Daicel.
The term room temperature means 20 to 25° C.
m.p. means melting point (n.d. means "not determined").
CC means column chromatography, hex stands for n-hexane, EA for ethyl acetate, ether for diethylether, iso for isopropanol and DEA for diethyl amine.

General Synthesis Specification 1

Grignard Reaction 1,2 molar equivalent magnesium chips were agitated in diethylether or tetrahydrofuran p.a. (about 1 ml of solvent per mmol of Mg). 1,2 molar equivalent of each halide, dissolved in 1 ml of solvent per mmol of halide, was added in drops so that the reaction mixture boiled slightly. After adding, it was agitated for one hour at room temperature. In the case of unsubstituted phenethyl Grignard, the Grignard reagent was optionally not usually produced, but a commercially available solution of phenethyl magnesium chloride was used (1 mol/l in tetrahydrofuran) (Sigma Aldrich GmbH, Deisenhofen, Germany). Next, 1 molar equivalent of each Mannich base was dissolved in 1.5 ml of solvent per mmol, dropped into the Grignard batch with ice-bath cooling and agitated for 15 hours at room temperature.

For processing, saturated ammonium chloride solution (1.5 ml per mmol of Mannich base) was added with ice-bath cooling and extracted three times at room temperature with diethylether (each time 1.5 ml per mmol of Mannich base). The combined organic extracts were dried over sodium sulphate, filtered and evaporated to low bulk on a rotary evaporator (500 to 10 mbar). For purification, the crude base produced was dissolved in 2-butanone (3 ml per mmol of crude product) and the corresponding hydrochloride was precipitated under agitation and with the addition of a half molar equivalent of water, followed by 1,1 molar equivalent of chlorotrimethylsilane.

If no hydrochloride was formed with cooling to about 4° C. and agitation overnight or after adding ether, the precipitation batch was taken up in double the volume of water, washed with three small portions of ether, the aqueous phase made alkali with a little approximately 30% sodium hydroxide solution and extracted three times with ether. These last extracts were again combined and either passed directly to another hydrochloride precipitation or first purified by column chromatography on silica gel.

General Synthesis Specification 2
Semi-automated Grignard Reaction 1

As described in general synthesis specification 1, in each case, halide and magnesium chips were used to produce each Grignard solution in tetrahydrofuran (theoretical content of Grignard reagent 1 mmol/l). In a nitrogen atmosphere, 4.0 ml of this solution was pipetted into a closed tube with a septum cap. It was cooled to −20° C. and, under agitation, 2.0 ml of the solution was added to a Mannich base in tetrahydrofuran (concentration 1.60 mmol/l). It was then warmed to room temperature and agitated overnight, next re-cooled to −20° C. and 2.0 ml of half-saturated ammonium chloride solution was added for hydrolysis.

Further processing was in accordance with general synthesis specification 1.

Example 1

2-(dimethylaminophenylmethyl)-1-phenethylcyclohexanol, hydrochloride

Example 2

2-[(2-chlorophenyl)dimethylaminomethyl]-1-phenethylcyclohexanol, hydrochloride

Example 3

2-[(2-bromophenyl)dimethylaminomethyl]-1-phenethylcyclohexanol, hydrochloride

Example 4

2-[dimethylamino-(3-methoxyphenyl)methyl]-1-phenethylcyclohexanol, hydrochloride Example 5

2-(dimethylamino-o-tolylmethyl)-1-phenethylcyclohexanol, hydrochloride

Example 6

2-(dimethylaminophenylmethyl)-1-(3-phenylpropyl)cyclohexanol, hydrochloride

Example 7

2-(dimethylaminophenylmethyl)-1-[2-(2-fluorophenyl)ethyl]cyclohexanol, hydrochloride Example 8

2-[dimethylamino-(2-fluorophenyl)methyl]-1-phenethylcyclohexanol, hydrochloride

Example 9

2-[(2-chlorophenyl)dimethylaminomethyl]-1-[2-(4-fluorophenyl)ethyl]cyclohexanol, hydrochloride Example 10

2-[(2-chlorophenyl)dimethylaminomethyl]-1-[2-(2-fluorophenyl)ethyl]cyclohexanol, hydrochloride Example 11

2-[(2-chlorophenyl)dimethylaminomethyl]-1-[2-(3-fluorophenyl)ethyl]cyclohexanol, hydrochloride Example 12

1-[2-(2-chlorophenyl)ethyl]-2-(dimethylaminophenylmethyl)cyclohexanol, hydrochloride Example 13

1-[2-(3-chlorophenyl)ethyl]-2-(dimethylaminophenylmethyl)cyclohexanol, hydrochloride Example 14

1-phenethyl-2-(phenylpiperidine-1-yl-methyl)cyclohexanol, hydrochloride

Example 15

1-[2-(2-chlorophenyl)ethyl]-2-(dimethylamino-o-tolylmethyl)cyclohexanol, hydrochloride Example 16

1-[2-(3-chlorophenyl)ethyl]-2-(dimethylamino-o-tolylmethyl)cyclohexanol, hydrochloride Example 17

2-[dimethylamino-(2-fluorophenyl)methyl]-1-[2-(4-fluorophenyl)ethyl]cyclohexanol, hydrochloride Example 18

2-(dimethylamino-o-tolylmethyl)-1-[2-(4-fluorophenyl)ethyl]cyclohexanol, hydrochloride Example 19

1-[2-(2-chlorophenyl)ethyl]-2-(dimethylamino-(2-fluorophenyl)methyl]cyclohexanol, hydrochloride Example 20

1-[2-(2-chlorophenyl)ethyl]-2-(dimethylamino-m-tolylmethyl)cyclohexanol, hydrochloride Example 21

1-[2-(3-chlorophenyl)ethyl]-2-(dimethylamino-(2-fluorophenyl)methyl]cyclohexanol, hydrochloride Example 22

1-[2-(2-chlorophenyl)ethyl]-2-(dimethylamino-(3-fluorophenyl)methyl]cyclohexanol, hydrochloride Example 23

1-[2-(2-chlorophenyl)ethyl]-2-(pyrrolidine-1-yl-o-tolylmethyl)cyclohexanol, hydrochloride

Example 24

1-[2-(2-chlorophenyl)ethyl]-2-(morpholine-4-yl-o-tolylmethyl)cyclohexanol, hydrochloride

Example 25

1-[2-(2-chlorophenyl)ethyl]-2-(piperidine-1-yl-o-tolylmethyl)cyclohexanol, hydrochloride

Example 26

1-[2-(3-chlorophenyl)ethyl]-2-(dimethylamino-o-tolylmethyl)cyclohexanol, hydrochloride

Example 27

2-[dimethylamino-(2-trifluoromethylphenyl)methyl]-1-phenethylcyclohexanol, hydrochloride

Example 28

2-[dimethylamino-(2-methoxyphenyl)methyl]-1-[2-(2-fluorophenyl)ethyl]cyclohexanol, hydrochloride

Example 29

2-[dimethylamino-(2-fluorophenyl)methyl]-1-[2-(2-fluorophenyl)ethyl]cyclohexanol, hydrochloride

Example 30

2-(dimethylamino-o-tolylmethyl)-1-[2-(2-fluorophenyl)ethyl]cyclohexanol, hydrochloride

Example 31

1-[2-(2-fluorophenyl)ethyl]-2-(pyrrolidine-1-yl-o-tolylmethyl)cyclohexanol, hydrochloride

Example 32

2-[(2-bromophenyl)dimethylaminomethyl]-1-[2-(2-chlorophenyl)ethyl]cyclohexanol, hydrochloride

Example 33

2-[(2-chlorophenyl)dimethylaminomethyl]-1-[2-(2-chlorophenyl)ethyl]cyclohexanol, hydrochloride

Example 34

2-[(2-bromophenyl)dimethylaminomethyl]-1-[2-(2-fluorophenyl)ethyl]cyclohexanol, hydrochloride

Example 35

2-[(2-chlorophenyl)dimethylaminomethyl]-1-(2-o-tolylethyl)cyclohexanol, hydrochloride

Example 36

2-[(2-chlorophenyl)dimethylaminomethyl]-1-(3-phenylpropyl)cyclohexanol, hydrochloride

Example 37

2-(dimethylaminophenylmethyl)-1-(2-o-tolylethyl)cyclohexanol, hydrochloride

Example 38

2-[(2-bromophenyl)dimethylaminomethyl]-1-(2-o-tolylethyl)cyclohexanol, hydrochloride

Example 39

2-(dimethylamino-o-tolylmethyl]-1-(2-o-tolylethyl)cyclohexanol, hydrochloride

Example 40

2-[(2-bromophenyl)dimethylaminomethyl]-1-(3-phenylpropyl)cyclohexanol, hydrochloride

Example 41

2-[(2-chloro4-fluorophenyl)dimethylaminomethyl]-1-[2-(2-fluorophenyl)ethyl]cyclohexanol, hydrochloride

Example 42

2-[(2-chloro4-fluorophenyl)dimethylaminomethyl]-1-[2-(2-chlorophenyl)ethyl]cyclohexanol, hydrochloride

Example 43

2-[dimethylamino-(2-fluorophenyl)methyl]-1-(2-o-tolylethyl)cyclohexanol, hydrochloride

Example 44

2-[dimethylamino-(2-fluorophenyl)methyl]-1-(3-phenylpropyl)cyclohexanol, hydrochloride

Example 45

2-(dimethylamino-o-tolylmethyl)1-(3-phenylpropyl)cyclohexanol, hydrochloride

Example 46

1-[2-(2-chlorophenyl)ethyl]-2-[dimethylamino-(2-trifluoromethylphenyl)methyl]cyclohexanol, hydrochloride

Example 47

2-[dimethylamino-(2-trifluoromethylphenyl)methyl]-1-[2-(2-fluorophenyl)ethyl]cyclohexanol, hydrochloride The Mannich bases used in examples 1 to 47 and the quantities of them, each halide used and the yields for each of the example compounds obtained in accordance with general synthesis specification 1 or 2, the processing of them and their melting points are given in Table 1 below.

TABLE 1

Synthesis of selected 1-amino-6-phenylhexane-3-ol
or 1-amino-6-phenylhexane-3-ol compounds.

| Example No | Batch size mmol of Mannich base | Mannich base | Halide | Yield (m.p.) g of hydrochloride | Purification |
|---|---|---|---|---|---|
| 1 | 13.0 | 2-(dimethyl-aminophenyl-methyl)cyclo-hexanone | Phenethyl-bromide | 3.26 (100° C.)* | Addition of ether |
| 2** | 7.47 | 2-[(2-chloro-phenyl)dimethyl-aminomethyl]-cyclohexanone | Phenethyl-chloride | 1.12 (110° C.)* | 4° C. |
| 3** | 6.99 | 2-[(2-bromo-phenyl)dimethyl-aminomethyl]-cyclohexanone | Phenethyl-chloride | 1.13 (162–165° C.) | 4° C. |
| 4** | 11.5 | 2-[dimethyl-amino-(3-methoxyphenyl)-methyl]cyclo-hexanone | Phenethyl-chloride | 3.81 (90° C.)* | Addition of ether |
| 5** | 10.2 | 2-(dimethyl-amino-o-tolyl-methyl)cyclo-hexanone | Phenethyl-chloride | 2.09 (187–188° C.) | 4° C. |
| 6 | 10.8 | 2-(dimethyl-aminophenyl-methyl)cyclo-hexanone | 1-bromo-3-phenyl-propane | 2.92 (90° C.)* | Addition of ether |
| 7 | 10.8 | 2-(dimethyl-aminophenyl-methyl)cyclo-hexanone | 1-(2-bromo-ethyl)-2-fluorobenzene | 2.59 (95° C.)* | Addition of ether |
| 8** | 8.02 | 2-[dimethyl-amino-(2-fluorophenyl)-methyl]cyclo-hexanone | Phenethyl-chloride | 1.21 (172–174° C.) | Second precipitation |
| 9 | 7.52 | 2-[(2-chloro-phenyl)dimethyl-aminomethyl]-cyclohexanone | 1-(2-bromo-ethyl)-4-fluorobenzene | 1.74 (170° C.)* | 4° C. |
| 10 | 22.6 | 2-[(2-chloro-phenyl)dimethyl-aminomethyl]-cyclohexanone | 1-(2-bromo-ethyl)-2-fluorobenzene | 3.51 (162–163° C.) | CC (hex/ether 2/1) |
| 11 | 7.52 | 2-[(2-chloro-phenyl)dimethyl-aminomethyl]-cyclohexanone | 1-(2-bromo-ethyl)-3-fluorobenzene | 0.24 (120–126° C.) | CC (hex/EA 4/1) |
| 12 | 86.4 | 2-(dimethyl-aminophenyl-methyl)cyclo-hexanone | 1-(2-bromo-ethyl)-2-chlorobenzene | 3.31 (152° C.)* | CC (hex/ether 1/1) |
| 13 | 8.64 | 2-(dimethyl-aminophenyl-methyl)cyclo-hexanone | 1-(2-bromo-ethyl)-3-chlorobenzene | 0.84 (95° C.)* | Second precipitation |
| 14** | 7.37 | 2-(phenyl-piperidine-1-yl-methyl)cyclo-hexanone | Phenethyl-chloride | 1.19 (127° C.)* | Second precipitation |
| 15 | 40.8 | 2-(dimethyl-amino-o-tolyl-methyl)cyclo-hexanone | 1-(2-bromo-ethyl)-2-chlorobenzene | 3.20 (190–194° C.) | CC (hex/ether 1/1) |
| 16*** | 3.19 | 2-(dimethyl-amino-o-tolyl-methyl)cyclo-hexanone | 1-(2-bromo-ethyl)-3-chlorobenzene | 0.32 (n.d.) | 4° C. |
| 17*** | 3.19 | 2-[dimethyl-amino-(2-fluorophenyl)-methyl]cyclo-hexanone | 1-(2-bromo-ethyl)-4-fluorobenzene | 0.73 (n.d.) | 4° C. |
| 18*** | 3.19 | 2-(dimethyl-amino-o-tolyl-methyl)cyclo-hexanone | 1-(2-bromo-ethyl)-4-fluorobenzene | 0.57 (n.d.) | 4° C. |

TABLE 1-continued

Synthesis of selected 1-amino-6-phenylhexane-3-ol
or 1-amino-6-phenylhexane-3-ol compounds.

| Example No | Batch size mmol of Mannich base | Mannich base | Halide | Yield (m.p.) g of hydrochloride | Purification |
|---|---|---|---|---|---|
| 19*** | 3.19 | 2-[dimethyl-amino-(2-fluorophenyl)-methyl]cyclo-hexanone | 1-(2-bromo-ethyl)-2-chlorobenzene | 0.50 (213° C.) | Second precipitation |
| 20*** | 3.19 | 2-(dimethyl-amino-m-tolyl-methyl)cyclo-hexanone | 1-(2-bromo-ethyl)-2-chlorobenzene | 0.47 (n.d.) | Second precipitation |
| 21*** | 3.19 | 2-[dimethyl-amino-(2-fluorophenyl)-methyl]cyclo-hexanone | 1-(2-bromo-ethyl)-3-chlorobenzene | 0.63 (n.d.) | Second precipitation |
| 22*** | 3.19 | 2-[(dimethyl-amino-(3-fluorophenyl)-methyl]cyclo-hexanone | 1-(2-bromo-ethyl)-2-chlorobenzene | 0.66 (n.d.) | Second precipitation |
| 23 | 36.8 | 2-(pyrrolidine-1-yl-o-tolylmethyl)-cyclohexanone | 1-(2-bromo-ethyl)-2-chlorobenzene | 2.18 (155° C.)* | CC (hex/ether 1/1) |
| 24*** | 3.19 | 2-(morpholine-4-yl-o-tolylmethyl)-cyclohexanone | 1-(2-bromo-ethyl)-2-chlorobenzene | 0.37 (n.d.) | Second precipitation |
| 25*** | 3.19 | 2-(piperidine-1-yl-o-tolylmethyl)-cyclohexanone | 1-(2-bromo-ethyl)-2-chlorobenzene | 0.27 (n.d.) | Second precipitation |
| 26*** | 3.19 | 2-(dimethyl-amino-o-tolyl-methyl)cyclo-hexanone | 1-(2-bromo-ethyl)-3-chlorobenzene | 0.24 (n.d.) | Fourth precipitation |
| 27** | 8.35 | 2-[(dimethyl-amino-(3-trifluoromethyl-phenyl)methyl]-cyclohexanone | Phenethyl-chloride | 2.26 (n.d.) | 4° C. |
| 28 | 9.56 | 2-[(dimethyl-amino-(2-methoxyphenyl)-methyl]cyclo-hexanone | 1-(2-bromo-ethyl)-2-fluorobenzene | 0.49 (n.d.) | CC (ether) |
| 29 | 10.0 | 2-[(dimethyl-amino-(2-fluorophenyl)-methyl]cyclo-hexanone | 1-(2-bromo-ethyl)-2-fluorobenzene | 1.53 (n.d.) | CC (hex/ether 1/1) |
| 30 | 10.2 | 2-(dimethyl-amino-o-tolyl-methyl)-cyclohexanone | 1-(2-bromo-ethyl)-2-fluorobenzene | 0.52 (n.d.) | CC (hex/ether 1/1) |
| 31 | 9.21 | 2-(pyrrolidine-1-yl-o-tolylmethyl)-cyclohexanone | 1-(2-bromo-ethyl)-2-fluorobenzene | 0.63 (n.d.) | CC (hex/ether 1/1) |
| 32 | 16.1 | 2-[(2-bromo-phenyl)dimethyl-aminomethyl]-cyclohexanone | 1-(2-bromo-ethyl)-2-chlorobenzene | 3.22 (n.d.) | CC (hex/ether 1/1) |
| 33 | 18.8 | 2-[(2-chloro-phenyl)dimethyl-aminomethyl]-cyclohexanone | 1-(2-bromo-ethyl)-2-chlorobenzene | 3.08 (n.d.) | CC (hex/ether 1/1) |
| 34 | 16.1 | 2-[(2-bromo-phenyl)dimethyl-aminomethyl]-cyclohexanone | 1-(2-bromo-ethyl)-2-fluorobenzene | 1.54 (n.d.) | CC (hex/ether 1/1) |
| 35 | 18.8 | 2-[(2-chloro-phenyl)dimethyl-aminomethyl]-cyclohexanone | 1-(2-bromo-ethyl)-2-methylbenzene | 1.17 (n.d.) | CC (hex/ether 2/1) |
| 36 | 18.8 | 2-[(2-chloro-phenyl)dimethyl-aminomethyl]-cyclohexanone | 1-bromo-3-phenyl-propane | 1.11 (n.d.) | CC (hex/ether 1/1) |
| 37 | 20.1 | 2-(dimethyl-aminophenyl-methyl)-cyclohexanone | 1-(2-bromo-ethyl)-2-methylbenzene | 1.30 (n.d.) | CC (hex/ether 1/1) |

TABLE 1-continued

Synthesis of selected 1-amino-6-phenylhexane-3-ol or 1-amino-6-phenylhexane-3-ol compounds.

| Example No | Batch size mmol of Mannich base | Mannich base | Halide | Yield (m.p.) g of hydrochloride | Purification |
|---|---|---|---|---|---|
| 38 | 16.1 | 2-[(2-bromo-phenyl)dimethyl-aminomethyl]-cyclohexanone | 1-(2-bromo-ethyl)-2-methylbenzene | 3.34 (n.d.) | CC (hex/ether 2/1) |
| 39 | 20.4 | 2-(dimethyl-amino-o-tolylmethyl)-cyclohexanone | 1-(2-bromo-ethyl)-2-methylbenzene | 1.44 (n.d.) | CC (hex/ether 1/1) |
| 40 | 16.1 | 2-[(2-bromo-phenyl)dimethyl-aminomethyl]-cyclohexanone | 1-bromo-3-phenyl-propane | 3.82 (n.d.) | CC (hex/ether 2/1) |
| 41 | 17.6 | 2-[(2-chloro-4-fluorophenyl)-dimethylamino-methyl]-cyclohexanone | 1-(2-bromo-ethyl)-2-fluorobenzene | 0.90 (n.d.) | CC (hex/ether 2/1) |
| 42 | 17.6 | 2-[(2-chloro-4-fluorophenyl)-dimethylamino-methyl]-cyclohexanone | 1-(2-bromo-ethyl)-2-chlorobenzene | 0.88 (n.d.) | CC (hex/ether 2/1) |
| 43 | 20.1 | 2-[(dimethyl-amino-(2-fluorophenyl)-methyl]cyclo-hexanone | 1-(2-bromo-ethyl)-2-methylbenzene | 0.79 (n.d.) | CC (hex/ether 2/1) |
| 44 | 20.1 | 2-[(dimethyl-amino-(2-fluorophenyl)-methyl]cyclo-hexanone | 1-bromo-3-phenyl-propane | 4.08 (n.d.) | CC (hex/ether 2/1) |
| 45 | 20.4 | 2-(dimethyl-amino-o-tolylmethyl)-cyclohexanone | 1-bromo-3-phenyl-propane | 0.63 (n.d.) | CC (EA) |
| 46 | 16.7 | 2-[(dimethyl-amino-(2-trifluoromethyl)-phenyl)methyl]-cyclohexanone | 1-(2-bromo-ethyl)-2-chlorobenzene | 2.08 (n.d.) | CC (hex/ether 2/1) |
| 47 | 16.7 | 2-[(dimethyl-amino-(2-trifluoromethyl)-phenyl)methyl]-cyclohexanone | 1-(2-bromo-ethyl)-2-fluorobenzene | 2.06 (n.d.) | CC (hex/ether 2/1) |

*From this temperature, decomposition of the compound was observed.
**A commercially available solution of phenethyl magnesium chloride in tetrahydrofuran was used.
***Carried out in accordance with general synthesis specification 2.

Resolutions of Racemates

With some of the racemic substances, a racemic resolution was carried out by means of preparative HPLC and then the fractions obtained were precipitated in accordance with general synthesis specification 1 as hydrochloride. The elution medium used was a mixture of hexane, isopropanol and diethylamine. The resolution conditions are summarised below:

Example 15

| Preparative resolution: | |
|---|---|
| Elution medium | Hex/iso/DEA 980:20:1 |
| Column | ChiraPak AD (10 μm) 250 × 20 mm |
| Sample | 5 percent by mass in elution medium/iso 1:1; 2 ml sample volume per injection |
| Flow | 9 ml/min |
| Detection | 254 nm |

| Analytical resolution: | |
|---|---|
| Elution medium | Hex/iso/DEA 980:20:1 |
| Column | ChiraPak AD (10 μm) 250 × 4.6 mm |
| Sample | 0.1 percent by mass in elution medium; 20 μl sample volume |
| Flow | 1 ml/min |
| Detection | 235 nm |
| Fraction 1: | |

Example 48

(−)-15-1-[2-(2-chlorophenyl)ethyl]-2-(dimethylamino-o-tolylmethylcyclohexanol), hydrochloride
Fraction 2

Example 49

(+)-15-1-[2-(2-chlorophenyl)ethyl]-2-(dimethylamino-o-tolylmethylcyclohexanol), hydrochloride

Example 6

Preparative resolution:

| | |
|---|---|
| Elution medium | Hex/iso/DEA 970:30:1 |
| Column | Chiracel OD (10 μm) 250 × 20 mm |
| Sample | 5 percent by mass in elution medium; 1 ml sample volume per injection |
| Flow | 9 ml/min |
| Detection | 241 nm |

Analytical resolution:

| | |
|---|---|
| Elution medium | Hex/iso/DEA 970:30:1 |
| Column | Chiracel OD (10 μm) 250 × 4.6 mm |
| Sample | 0.1 percent by mass in elution medium; 20 μl sample volume |
| Flow | 1 ml/min |
| Detection | 241 nm |

Fraction 1:

Example 50

(−)-2-(dimethylaminophenylmethyl)1-(3-phenylpropyl) cyclohexanol, hydrochloride

Fraction 2

Example 51

(+)-2-(dimethylaminophenylmethyl)-1-(3-phenylpropyl) cyclohexanol, hydrochloride

Example 10

Preparative resolution:

| | |
|---|---|
| Elution medium | Hex/iso/DEA 850:150:1 |
| Column | Chiracel OD (10 μm) 250 × 25 mm |
| Sample | 5 percent by mass in elution medium; 2 ml sample volume per injection |
| Flow | 9 ml/min |
| Detection | 247 nm |

Analytical resolution:

| | |
|---|---|
| Elution medium | Hex/iso/DEA 850:150:1 |
| Column | Chiracel OD (10 μm) 250 × 4.6 mm |
| Sample | 0.1 percent by mass in elution medium; 20 μl sample volume |
| Flow | 1 ml/min |
| Detection | 247 nm |

Fraction 1:

Example 52

(−)-2-[(2-chlorophenyl)dimethylaminomethyl]-1-[2-(2-fluorophenyl)ethyl]cyclohexanol, hydrochloride Fraction 2

Example 53

(+)-2-[(2-chlorophenyl)dimethylaminomethyl]-1-[2-(2-fluorophenyl)ethyl]cyclohexanol, hydrochloride The excess of enantiomers (ea in %) and the specific angle of rotation of the enantiomers obtained are given in Table 2 below.

TABLE 2

Enantiomeric excess (ee in %) and specific angle of rotation of the enantiomers

| Example No | Enantiomeric excess ee/% | Specific angle of rotation $\alpha D^{20}$ in methanol |
|---|---|---|
| 48 | >98 | −34.1 (c = 0.935) |
| 49 | >98 | +33.5 (c = 0.951) |
| 50 | >98 | −21.2 (c = 0.765) |
| 51 | >98 | +21.3 (c = 0.712) |
| 52 | >98 | −34.0 (c = 0.908) |
| 53 | >98 | +33.8 (c = 0.914) |

Molecular Biological Research

The affinity of each of these example compounds 1 to 53 to the (+)-MK801 binding site on the ionotropic NMDA receptor was determined in accordance with the procedure described above. The corresponding percentage inhibition of the specific binding of the ($^3$H)-(+)-MK801 ligand and the corresponding $K_i$ values are given in Table 3 below.

TABLE 3

Percentage inhibition of specific binding of the ($^3$H)-(+)-MK801 ligand and $K_i$ values

| Example | Percentage inhibition of ($^3$H)-(+)-MK801 binding at 10 μM | $K_i$/μM |
|---|---|---|
| 1 | 56 | 3.8 |
| 2 | 95 | 1.7 |
| 3 | 91 | 1.7 |
| 4 | 51 | 6.2 |
| 5 | 93 | 1.3 |
| 6 | 74 | 2.6 |
| 7 | 91 | 1.1 |
| 8 | 91 | 1.6 |
| 9 | 67 | 3.8 |
| 10 | 102 | 0.4 |
| 11 | 93 | 2.1 |
| 12 | 85 | 1.5 |
| 13 | 61 | 3.1 |
| 14 | 88 | 2.8 |
| 15 | 100 | 0.7 |
| 16 | 92 | 1.9 |
| 17 | 54 | 5.8 |
| 18 | 54 | 6.1 |
| 19 | 102 | 0.8 |
| 20 | 62 | 4.3 |
| 21 | 90 | 2.1 |
| 22 | 74 | 3.0 |
| 23 | 101 | 0.4 |
| 24 | 48 | 3.7 |
| 25 | 89 | 1.4 |
| 26 | 89 | 1.3 |
| 27 | 67 | 4.2 |
| 28 | 82 | 2.5 |
| 29 | 104 | 0.3 |
| 30 | 105 | 0.3 |
| 31 | 99 | 0.1 |
| 32 | 96 | 0.7 |
| 33 | 93 | 0.6 |
| 34 | 95 | 0.4 |
| 35 | 93 | 1.8 |
| 36 | 85 | 1.9 |
| 37 | 77 | 1.8 |
| 38 | 93 | 2.3 |
| 39 | 90 | 1.4 |
| 40 | 82 | 1.9 |
| 41 | 94 | 1.2 |
| 42 | 85 | 2.0 |
| 43 | 92 | 1.4 |
| 44 | 91 | 1.4 |
| 45 | 91 | 1.8 |
| 46 | 79 | 1.9 |

TABLE 3-continued

Percentage inhibition of specific binding of
the ($^3$H)-(+)-MK801 ligand and $K_i$ values

| Example | Percentage inhibition of ($^3$H)-(+)-MK801 binding at 10 μM | $K_i/\mu M$ |
|---|---|---|
| 47 | 90 | 1.4 |
| 48 | 99 | 0.4 |
| 49 | 93 | 1.3 |
| 50 | 87 | 0.6 |
| 51 | 80 | 2.3 |
| 52 | 105 | 0.2 |
| 53 | 104 | 0.5 |

What is claimed is:

1. A method of modifying the physiological or pathophysiological processes of a patient comprising administering to the patient a physiologically modifying amount of a compound having NMDA antagonistic effect and selected from the group consisting of substituted 1-amino-5-phenylpentane-3-ol and substituted 1-amino-6-phenylhexane-3-ol compound with general formula I,

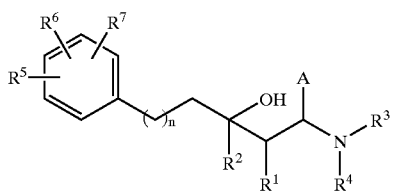

I where
n=1 or 2,
group A represents an optionally substituted aryl or heteroaryl group,
groups $R^1$ and $R^2$, the same or different, stand for a $C_{1-6}$ alkyl group or groups $R_1$ and $R^2$ together form a $(CH_2)_{2-6}$ chain, which may also be phenyl substituted or may be attached to a phenyl ring to form a bicyclic system in which the cyclic aliphatic moiety and the phenyl ring share two carbon atoms and groups $R^3$ to $R^8$ and A have the meaning according to general formula I,
groups $R^3$ and $R^4$, the same or different, stand for a $C_{1-6}$ alkyl group, an optionally substituted aryl group or an optionally substituted aryl group which is bound via a $C_{1-3}$ alkylene group, or groups $R^3$ and $R^4$ together represent $(CH_2)_{3-6}$ or $CH_2CH_2OCH_2CH_2$,
groups $R^5$, $R^6$ and $R^7$, the same or different, represent H, F, Cl, Br, I, $CF_3$, $OR^8$, $SO_2CH_3$, $SO_2CF_3$, phenyl, CN, $NO_2$ or a $C_{1-6}$ alkyl group,
group $R^8$ stands for H, a $C_{1-6}$ alkyl group, an optionally substituted aryl group, an optionally substituted heteroaryl group or for, an optionally substituted aryl or heteroaryl group which is bound via a $C_{1-3}$ alkylene group,
diastereomers of such compounds, enantiomers of such compounds, physiologically tolerable salts of such compounds, and mixtures thereof.

2. The method of claim 1 where $R^1$ and $R^2$, the same or different, are $C_{1-3}$-alkyl.

3. The method of claim 1 where $R^3$ and $R^4$, the same or different, are $C_{1-3}$-alkyl.

4. The method of claim 1 where $R^8$ is $C_{1-3}$-alkyl.

5. The method of claim 1 where $R^1$ and $R^2$ together form a $(CH_2)_{2-6}$ chain, which may also be phenyl substituted or may be attached to a phenyl ring. to form a bicyclic system in which the cyclic aliphatic moiety and the phenyl ring share two carbon atoms and groups $R^3$ to $R^8$ and A have the meaning according to general formula I.

6. The method of claim 1 where A is an unsubstituted or substituted phenyl, thiophenyl or furyl group.

7. The method of claim 1 where $R^5$ to $R^7$, the same or different, mean H, a halogen or a $CF_3$ group.

8. The method of claim 1 where $R^1$ and $R^2$ together form a cyclohexyl ring, which may also be phenyl substituted or may be attached to a phenyl ring to form a bicyclic system in which the cyclic aliphatic moiety and the phenyl ring share two carbon atoms, and A is a substituted or unsubstituted phenyl, thiophenyl or furyl.

9. The method of claim 1 where the phenyl ring of general formula I is substituted once or twice in an ortho-postition.

10. The method of claim 1 where A represents a phenyl ring, which is substituted once or twice in an ortho-position.

11. The method of claim 1 where A is phenyl, which is substituted once or twice in an ortho-position, the phenyl ring of general formula I is substituted once or twice in an ortho-position.

12. The method of claim 1 where the compound is selected from the group consisting of
2-(dimethylaminophenylmethyl)-1-phenethylcyclohexanol or the corresponding hydrochloride,
2-[(2-chlorophenyl)dimethylaminomethyl]-1-phenethylcyclohexanol or the corresponding hydrochloride,
2-[(2-bromophenyl)dimethylaminomethyl]-1-phenethylcyclohexanol or the corresponding hydrochloride,
2-[dimethylamino-(3-methoxyphenyl)methyl]-1-phenethylcyclohexanol or the corresponding hydrochloride,
2-(dimethylamino-o-tolylmethyl)-1-phenethylcyclohexanol or the corresponding hydrochloride
2-(dimethylaminophenylmethyl)-1-(3-phenylpropyl)cyclohexanol or the corresponding hydrochloride,
2-(dimethylaminophenylmethyl)-1-[2-(2-fluorophenyl)ethyl]cyclohexanol or the corresponding hydrochloride,
2-[dimethylamino-(2-fluorophenyl)methyl]-1-phenethylcyclohexanol or the corresponding hydrochloride,
2-[(2-chlorophenyl)dimethylaminomethyl]-1-[2-(4-fluorophenyl)ethyl]cyclohexanol or the corresponding hydrochloride,
2-[(2-chlorophenyl)dimethylaminomethyl]-1-[2-(2-fluorophenyl)ethyl]cyclohexanol or the corresponding hydrochloride,
2-[(2-chlorophenyl)dimethylaminomethyl]-1-[2-(3-fluorophenyl)ethyl]cyclohexanol or the corresponding hydrochloride,
1-[2-(2-chlorophenyl)ethyl]-2-(dimethylaminophenylmethyl)cyclohexanol or the corresponding hydrochloride,
1-[2-(3-chlorophenyl)ethyl]-2-(dimethylaminophenylmethyl)cyclohexanol or the corresponding hydrochloride,
1-phenethyl-2-(phenylpiperidine-1-yl-methyl)cyclohexanol or the corresponding hydrochloride,
1-[2-(2-chlorophenyl)ethyl]-2-(dimethylamino-o-tolylmethyl)cyclohexanol or the corresponding hydrochloride,
1-[2-(3-chlorophenyl)ethyl]-2-(dimethylamino-o-tolylmethyl)cyclohexanol or the corresponding hydrochloride, 2-[dimethylamino-(2-fluorophenyl)methyl]-1-[2-(4-fluorophenyl)ethyl]cyclohexanol or the corresponding hydrochloride, 2-(dimethylamino-o-tolylmethyl)1-[2-(4-fluorophenyl)ethyl]cyclohexanol or the corresponding hydrochloride, 1-[2-(2-chlorophenyl)ethyl]-2-(dimethylamino-(2-fluorophenyl)methyl]cyclohexanol or the corresponding hydrochloride, 1-[2-(2-chlorophenyl)ethyl]-2-(dimethylamino-m-tolylmethyl)cyclohexanol or the corresponding hydrochloride, 1-[2-(3-chlorophenyl)ethyl]-2-(dimethylamino-(2-fluorophenyl)methyl]cyclohexanol or the corresponding hydrochloride, 1-[2-(2-chlorophenyl)ethyl]-2-(dimethylamino-(3-fluorophenyl)methyl]cyclohexanol or the corresponding hydrochloride, 1-[2-(2-chlorophenyl)ethyl]-2-(pyrrolidine-1-yl-o-tolylmethyl)cyclohexanol or the corresponding hydrochloride, 1-[2-(2-chlorophenyl)ethyl]-2-(morpholine-4-yl-o-tolylmethyl)cyclohexanol or the corresponding hydrochloride, 1-[2-(2-chlorophenyl)ethyl]-2-(piperidine-1-yl-o-tolylmethyl)cyclohexanol or the corresponding hydrochloride, 1-[2-(3-chlorophenyl)ethyl]-2-(dimethylamino-o-tolylmethyl)cyclohexanol or the corresponding hydrochloride, 2-[dimethylamino-(2-trifluoromethylphenyl)methyl]-1-phenethylcyclohexanol or the corresponding hydrochloride, 2-[dimethylamino-(2-methoxyphenyl)methyl]-1-[2-(2-fluorophenyl)ethyl]cyclohexanol or the corresponding hydrochloride, 2-[dimethylamino-(2-fluorophenyl)methyl]-1-[2-(2-fluorophenyl)ethyl]cyclohexanol or the corresponding hydrochloride, 2-(dimethylamino-o-tolylmethyl)-1-[2-(2-fluorophenyl)ethyl]cyclohexanol or the corresponding hydrochloride, 1-[2-(2-fluorophenyl)ethyl]-2-(pyrrolidine-1-yl-o-tolylmethyl)cyclohexanol or the corresponding hydrochloride, 2-[(2-bromophenyl)dimethylaminomethyl]-1-[2-(2-chlorophenyl)ethyl]cyclohexanol or the corresponding hydrochloride, 2-[(2-chlorophenyl)dimethylaminomethyl]-1-[2-(2-chlorophenyl)ethyl]cyclohexanol or the corresponding hydrochloride, 2-[(2-bromophenyl)dimethylaminomethyl]-1-[2-(2-fluorophenyl)ethyl]cyclohexanol or the corresponding hydrochloride, 2-[(2-chlorophenyl)dimethylaminomethyl]-1-(2-o-tolylethyl)cyclohexanol or the corresponding hydrochloride, 2-[(2-chlorophenyl)dimethylaminomethyl]-1-(3-phenylpropyl)cyclohexanol or the corresponding hydrochloride, 2-(dimethylaminophenylmethyl)-1-(2-o-tolylethyl)cyclohexanol or the corresponding hydrochloride, 2-[(2-bromophenyl)dimethylaminomethyl]-1-(2-o-tolylethyl)cyclohexanol or the corresponding hydrochloride, 2-(dimethylamino-o-tolylmethyl)-1-(2-o-tolylethyl)cyclohexanol or the corresponding hydrochloride, 2-[(2-bromophenyl)dimethylaminomethyl]-1-(3-phenylpropyl)cyclohexanol or the corresponding hydrochloride, 2-[(2-chloro4-fluorophenyl)dimethylaminomethyl]-1-[2-(2-fluorophenyl)ethyl]cyclohexanol or the corresponding hydrochloride, 2-[(2-chloro4-fluorophenyl)dimethylaminomethyl]-1-[2-(2-chlorophenyl)ethyl]cyclohexanol or the corresponding hydrochloride, 2-[dimethylamino-(2-fluorophenyl)methyl]-1-(2-o-tolylethyl)cyclohexanol or the corresponding hydrochloride, 2-[dimethylamino-(2-fluorophenyl)methyl]-1-(3-phenylpropyl)cyclohexanol or the corresponding hydrochloride, 2-(dimethylamino-o-tolylmethyl)-1-(3-phenylpropyl)cyclohexanol or the corresponding hydrochloride, 1-[2-(2-chlorophenyl)ethyl]-2-[dimethylamino-(2-trifluoromethylphenyl)methyl]cyclohexanol or the corresponding hydrochloride, and 2-[dimethylamino-(2-trifluoromethylphenyl)methyl]-1-[2-(2-fluorophenyl)ethyl]cyclohexanol or the corresponding hydrochloride.

13. A method of treating cerebrovascular attacks (strokes) comprising administering an effective amount of at least one compound according to claim 1 to a patient in need thereof.

14. A method of treating epilepsy comprising administering an effective amount of at least one compound according to claim 1 to a patient in need thereof.

15. A method of treating neurodegenerative diseases comprising administering an effective amount of at least one compound according to claim 1 to a patient in need thereof.

16. A method of treating Alzheimer's disease comprising administering an effective amount of at least one compound according to claim 1 to a patient in need thereof.

17. A method of treating Huntington's disease comprising administering an effective amount of at least one compound according to claim 1 to a patient in need thereof.

18. A method of treating Parkinson's disease comprising administering an effective amount of at least one compound according to claim 1 to a patient in need thereof.

19. A method of treating cerebral ischaemia comprising administering an effective amount of at least one compound according to claim 1 to a patient in need thereof.

20. A method of treating cerebral infarcts comprising administering an effective amount of at least one compound according to claim 1 to a patient in need thereof.

21. A method of treating psychoses caused by raised amino acid level comprising administering an effective amount of use of at least one compound according to claim 1 to a patient in need thereof.

22. A method of treating cerebral oedema comprising administering an effective amount of at least one compound according to claim 1 to a patient in need thereof.

23. A method of treating under-supply of the central nervous system comprising administering an effective amount of at least one compound according to claim 1 to a patient in need thereof.

24. A method of treating hypoxia comprising administering an effective amount of at least one compound according to claim 1 to a patient in need thereof.

25. A method of treating anoxia comprising administering an effective amount of at least one compound according to claim 1 to a patient in need thereof.

26. A method of treating AIDS dementia comprising administering an effective amount of at least one compound according to claim 1 to a patient in need thereof.

27. A method of treating encephalomyelitis comprising administering an effective amount of at least one compound according to claim 1 to a patient in need thereof.

28. A method of treating Tourette's syndrome comprising administering an effective amount of at least one compound according to claim 1 to a patient in need thereof.

29. A method of treating perinatal asphyxia comprising administering an effective amount of at least one compound according to claim 1 to a patient in need thereof.

30. A method of treating tinnitus comprising administering an effective amount of at least one compound according to claim 1 to a patient in need thereof.

31. The method of claim 1 where the composition comprises a mixture of enantiomers of at least one compound according to general formula I where the enantiomers are not present in equimolar quantities.

32. The method of claim 31 where one of the enantiomers has a relative proportion of 5 to 45 percent by mass of the enantiomer mixture.

33. The method of claim 1 wherein groups $R^5$, $R^6$ and $R^7$, the same or different, represent a $C_{1-3}$ alkyl group.

\* \* \* \* \*